United States Patent [19]

Bollag et al.

[11] 3,950,418

[45] Apr. 13, 1976

[54] VITAMIN A ACID AMIDES

[75] Inventors: Werner Bollag, Basel; Rudolf Ruegg, Bottmingen; Gottlieb Ryser, Basel, all of Switzerland

[73] Assignee: Hoffmann-La Roche Inc., Nutley, N.J.

[22] Filed: Sept. 23, 1974

[21] Appl. No.: 503,559

Related U.S. Application Data

[60] Division of Ser. No. 354,026, April 24, 1973, abandoned, which is a continuation of Ser. No. 106,275, Jan. 13, 1971, abandoned.

[30] Foreign Application Priority Data

Feb. 2, 1970    Switzerland.......................... 1428/70

[52] U.S. Cl........ 260/557 R; 260/240 H; 260/240 J; 260/562 R; 424/248; 424/250; 424/267; 424/320

[51] Int. Cl.$^2$..................................... C07C 103/737
[58] Field of Search..................... 260/557 R, 561 N

[56] References Cited
UNITED STATES PATENTS
2,951,853    9/1960    Matsui................................. 260/557

OTHER PUBLICATIONS
Huisman et al. Received Trav. Chim Bays Bos 77 (1958) pp. 97–102.

*Primary Examiner*—Arthur P. Demers
*Attorney, Agent, or Firm*—Samuel L. Welt; Jon S. Saxe; R. Hain Swope

[57] ABSTRACT

Novel vitamin A acid amides and compositions thereof which are useful for the topical or systemic treatment of dermatological disorders.

8 Claims, No Drawings

VITAMIN A ACID AMIDES

RELATED APPLICATIONS

This application is a divisional application of U.S. patent application Ser. No. 354,026, filed April 24, 1973, now abandoned which in turn is a continuation application of U.S. patent application Ser. No. 106,275, filed Jan. 13, 1971, now abandoned.

SUMMARY OF THE INVENTION

In accordance with this invention, it has been found that compounds of the formula:

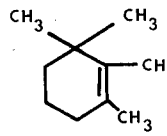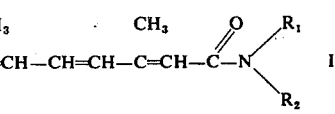 I wherein $R_1$ and $R_2$ are individually hydrogen, alkyl, lower alkoxy alkyl, lower alkylamino alkyl, hydroxy lower alkyl, lower alkenyl, phenyl, phenyl lower alkyl, cyclohexyl or cyclohexyl substituted with hydroxy lower alkyl, with at least one of $R_1$ or $R_2$ being other than hydrogen; and $R_1$ and $R_2$ taken together with the attached nitrogen atom forming a six membered heterocyclic ring containing at most one further oxygen or nitrogen hetero atom and at most substituted with one lower alkyl group; are useful in the treatment, by either systemic or topical modes, of certain disorders of the skin.

The compounds of formula I can be prepared through the reaction of vitamin A acid or a functional derivative thereof, preferably having the formula:

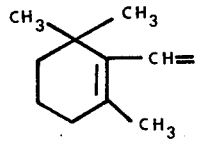 II wherein X is a hydroxy group, a halogen, or a lower alkoxy group; with a compound of the formula:

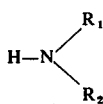 III wherein $R_1$ and $R_2$ are as above.

DETAILED DESCRIPTION OF THE INVENTION

As used throughout this application, the term "alkyl group" comprehends both straight-chain and branched hydrocarbon groups with 1 to 10 carbon atoms, such as methyl, ethyl, propyl, n-butyl, isopropyl, n-decyl and the like.

As used herein, the term "lower alkyl group" signifies both straight chain and branched chain hydrocarbon groups with 1 to 6 carbon atoms, such as methyl. The term "lower alkenyl group" signifies both straight chain and branched chain hydrocarbon groups with 2 to 6 carbon atoms, such as vinyl, allyl, etc. The term "hydroxy-lower alkyl group" signifies hydroxy-substituted lower alkyl groups with 1 to 6 carbon atoms such as, for example, hydroxyethyl, hydroxymethyl, etc. The term "phenyl-lower alkyl group" signifies phenyl substituted lower alkyl groups with 7 to 12 carbon atoms such as the benzyl or phenylethyl. The term "lower alkoxy group" signifies straight chain or branched alkoxy groups with 1 to 6 carbon atoms, for example, methoxy, ethoxy and the like. The term "lower alkylamino group" designates both mono and di-lower alkyl groups wherein lower alkyl is defined as above. Among the preferred lower alkylamino groups are included methylamino, N,N-dimethylamino, N,N-diethylamino, ethyl-amino and the like. As used herein, the term "$R_1$, $R_2$ taken together with the attached nitrogen atom forming a six-member heterocyclic ring" signifies saturated or unsaturated six-member rings which include at least the one nitrogen atom and which may further include an additional oxygen or nitrogen atom. Among the preferred heterocyclics are included piperidine, morpholine and piperazine.

The compounds of formula I are useful as medicaments for the topical and systemic therapy of acne, psoriasis and other related dermatological disorders which are characterized by an increased or pathologically altered cornification. They can also be used to treat disorders which are characterized by inflammatory or degenerative alterations of the mucous membranes.

Toxicity tests carried out in mice and rats gave the following results for acute toxicity:

A: Testing in the rat

Vitamin A acid ethyl amide in rape oil (per os and intraperitoneal administration)

|  | 24 hrs. (mg/kg) | 10 days (mg/kg) |
|---|---|---|
| $LD_{10}$ | >4000 | >4000 |
| $LD_{50}$ | >4000 | >4000 |
| $LD_{90}$ | >4000 | >4000 |

B: Testing in the Mouse

1. Vitamin A acid ethyl amide in rape oil (per os and intraperitoneal administration)

|  | 24 hrs. (mg/kg) | 10 days (mg/kg) | 20 days (mg/kg) |
|---|---|---|---|
| $LD_{10}$ | >4000 | >4000 | >4000 |
| $LD_{50}$ | >4000 | >4000 | >4000 |
| $LD_{90}$ | >4000 | >4000 | >4000 |

2. Vitamin A acid ethanol amide in rape oil (intraperitoneal administration)

|      | 24 hrs. (mg/kg) | 10 days (mg/kg) |
|------|-----------------|-----------------|
| $LD_{10}$ | >4000 | 710 |
| $LD_{50}$ | >4000 | 1000 |
| $LD_{90}$ | >4000 | 1400 |

3. Vitamin A acid diethyl amide, vitamin A acid n-butyl amide, vitamin A acid phenyl amide, vitamin A acid isopropyl amide, or vitamin A acid methyl amide in rape oil (intraperitoneal administration)

|      | 24 hrs. (mg/kg) | 10 days (mg/kg) |
|------|-----------------|-----------------|
| $LD_{10}$ | >4000 | >4000 |
| $LD_{50}$ | >4000 | >4000 |
| $LD_{90}$ | >4000 | >4000 |

The substituted vitamin A acid amides of formula I of the instant invention have a marked epithelium-protecting action (determined in accordance with Boguth et al. Int. Z. Vitaminf. 1960, 31 6), but in contrast to the free vitamin A acid and the unsubstituted amide they cause no skin irritation and no so-called A-hypervitaminosis.

The compounds of formula I of the instant invention are utilized in pharmaceutical preparations. In such preparations, these compounds are combined with a non-toxic, inert, solid or liquid carrier material. Suitable pharmaceutical carriers for enteral administration include tablets, capsules, dragees, syrups, suspensions, solutions, suppositories and the like. Parenteral dosage forms may be infusions or injectable solutions which can be injected intraveneously or intramuscularly.

In the preparation of pharmaceutical preparations, the preferred compounds of formula I to be utilized as the active ingredient are the vitamin A acid lower alkyl amides, such as, for example, the vitamin A acid monoethyl and diethylamides. Especially preferred is the vitamin A acid monoethyl amide.

The dosages contemplated for the use of the compound of the present invention varies according to the kind and route of application and according to the requirements of the patient. The compounds of formula I can be administered in amounts of up to 1000 mg. daily in one or more doses. A preferred form of pharmaceutical preparation is capsules with a content of about 50 mg. to about 200 mg. of active substance. Capsules of hard or soft gelatin, methyl cellulose or of other suitable materials which dissolve in the digestive tract are suitable.

The pharmaceutical preparations containing the compound of formula I can also contain inert as well as medicinally active additives. Tablets or granules, for example, can contain suitable binding agents, fillers, carriers or diluents. Liquid agents can, for example, exist in the form of a sterile, water-miscible solution. Besides the active substance, capsules can additionally contain a filling material or thickening agent. Furthermore, there can also be present flavor-improving additives, preservatives, stabilizing agents, moisture-retaining agents or emulsifiers, salts for varying the osmotic pressure, buffers and other additives as recognized in the art of pharmaceutical compounding.

The pharmaceutically acceptable carriers and diluents mentioned hereinbefore can be organic or inorganic substances, for example, water gelatin, lactose, starches, magnesium sterate, talc, gum arabic, polyalkylene glycols and the like.

For topical application, the compounds of formula I can expediently be used in the form of ointments, tinctures, creams, solutions, lotions, sprays, suspensions and the like. Ointments and creams, as well as solutions, are preferred. These preparations serving for topical application can be manufactured by mixing the process products as the active ingredient with non-toxic, inert solid or liquid carriers suitable for the topical administration of medicinal agents by methods according to the art of pharmaceutical compounding. The preparations for topical application contain from about 1% to about 10% by weight, preferably from about 2% to about 5% by weight of the active substance.

It is within the purview of the instant invention to incorporate into pharmaceutical preparations containing the active compounds enumerated herein an antioxidant such as, for example, tocopherols, N-methyl-$\gamma$-tocopheramine, as well as butylated hydroxyanisole, butylated hydroxytoluene or ethoxyquin.

The vitamin A acid amides of formula I of the instant invention can be prepared by reacting a vitamin A acid or a functional derivative thereof, preferably a compound of formula II with a compound of formula III. The especially preferred reactants are a vitamin A acid chloride and mono-ethyl amine. The reaction is expediently carried out in an conventional inert organic solvent, preferably diethylether. In carrying out this reaction, temperature and pressure are not critical, and this reaction can be carried out at room temperature and atmospheric pressure. Generally, however, a temperature of between about 20°C. and the reflux temperature of the reaction mixture is preferred. The reaction is also expediently carried out under an inert gas atmosphere, such as under nitrogen.

The following examples are illustrative but not limitative of this invention. All temperatures are in degrees centigrade.

EXAMPLE 1

Sixty parts by weight of ethylamine and 300 parts by volume of absolute diethyl ether are stirred with ice-cooling under a nitrogen atmosphere. 30 parts by weight of vitamin A acid chloride in 100 volume parts of absolute diethyl ether is added dropwise over a 30 minute period. The mixture is stirred at room temperature for 4 hours and further stirred for 2 hours under reflux. The mixture is then cooled, diluted with 1000 parts by volume of diethyl ether and washed four times with 100 parts by volume of water each time. The ether solution is dried over sodium sulphate, and the solvent is evaporated off. The residue is dissolved in and crystallized from a benzene-hexane mixture. There is obtained vitamin A acid monoethyl amide with a melting point of 137°–138°C; $\lambda_{max} = 347$ m$\mu$, $E_{1\ cm}^{1\%}$ 1540.

EXAMPLE 2

By utilizing the procedure of Example 1, vitamin A acid chloride is converted into the following vitamin A acid amides:

vitamin A acid methyl amide
m.p. 174°–175°C; $\lambda_{max}$ 345 m$\mu$, $E_{1\ cm}^{1\%}$ 1645;
vitamin A acid isopropyl amide m.p. 134°–135°C; $\mu_{max}$ 345 m$\mu$, $E_1{}_{cm}{}^{1\%}$ 1515;
vitamin A acid butyl amide
m.p. 92°–93°C; $\lambda_{max}$ 347 m$\mu$, $E_1{}_{cm}{}^{1\%}$ 1430;
vitamin A acid methyl propyl amide
m.p. 112°–113°C; $\lambda_{max}$ 347 m$\mu$, $E_1{}_{cm}{}^{1\%}$ 1462;
vitamin A acid n-decyl amide
m.p. 71°–72°C; $\lambda_{max}$ 347 m$\mu$, $E_1{}_{cm}{}^{1\%}$ 1163;
vitamin A acid ethanol amide
m.p. 138°–139°C; $\lambda_{max}$ 347 m$\mu$, $E_1{}_{cm}{}^{1\%}$ 1475;
vitamin A acid allyl amide
m.p. 126°–127°C; $\lambda_{max}$ 347 m$\mu$, $E_1{}_{cm}{}^{1\%}$ 1515;
vitamin A acid phenyl amide
m.p. 146°–147°C; $\lambda_{max}$362 m$\mu$, $E_1{}_{cm}{}^{1\%}$ 1450;
vitamin A acid diphenyl amide
m.p. 116°–117°C; $\lambda_{max}$368 m$\mu$, $E_1{}_{cm}{}^{1\%}$ 1130;
vitamin A acid benzyl amide
m.p. 104°–105°C; $\lambda_{max}$350 m$\mu$, $E_1{}_{cm}{}^{1\%}$ 1220;
vitamin A acid cyclohexyl amide
m.p. 158°–159°C; $\lambda_{max}$347 m$\mu$, $E_1{}_{cm}{}^{1\%}$ 1340;
vitamin A acid morpholide
m.p. 75°–76°C; $\lambda_{max}$340 m$\mu$, $E_1{}_{cm}{}^{1\%}$ 1230;
vitamin A acid piperidide
m.p. 94°–95°C; $\lambda_{max}$336 m$\mu$, $E_1{}_{cm}{}^{1\%}$ 1305;
vitamin A acid dicyclohexyl amide
m.p. 117°–118°C; $\lambda_{max}$347 m$\mu$, $E_1{}_{cm}{}^{1\%}$ 1122;
vitamin A acid 2-diethylaminoethyl amide
m.p. 86°–87°C; $\lambda_{max}$347 m$\mu$, $E_1{}_{cm}{}^{1\%}$ 1310;
vitamin A acid 2-methoxyethyl amide
m.p. 86°C; $\lambda_{max}$348 m$\mu$, $E_1{}_{cm}{}^{1\%}$ 1352; and
vitamin A acid N-methylpiperazide
m.p. 106°–107°C; $\lambda_{max}$342 m$\mu$, $E_1{}_{cm}{}^{1\%}$ 1163.

EXAMPLE 3

By utilizing the procedure of Example 1, vitamin A acid chloride is converted into vitamin A acid diethyl amide. For purification, the substance is chromatographed on 600 g of aluminium oxide (activity III neutral) by means of hexane, the pure amide passing through with hexane after a pre-fraction has been separated off. After removal of the solvent, vitamin A acid diethyl amide is obtained in the form of an oil $\lambda_{max}$340 m$\mu$, $E_1{}_{cm}{}^{1\%}$ 1300.

EXAMPLE 4

By utilizing the procedure of Examples 1 and 3 vitamin A acid chloride is converted into the following vitamin A acid amides:
vitamin A acid di-n-butyl amide
$\lambda_{max}$337 m$\mu$, $E_1{}_{cm}{}^{1\%}$ 985;
vitamin A acid diallyl amide
$\lambda_{max}$338 m$\mu$, $E_1{}_{cm}{}^{1\%}$ 1200;
vitamin A acid di-n-decyl amide
$\lambda_{max}$337 m$\mu$, $E_1{}_{cm}{}^{1\%}$ 775; and
vitamin A acid 2-hydroxyethyl cyclohexyl amide
$\lambda_{max}$338 m$\mu$, $E_1{}_{cm}{}^{1\%}$ 1100.

EXAMPLE 5

A 2% ointment with the following composition is prepared in accordance with the art of pharmaceutical compounding:

| Ingredient | Weight in Grams |
|---|---|
| Vitamin A acid ethyl amide | 2.0 |
| Cetyl alcohol | 2.4 |
| Lanolin | 6.0 |
| White petroleum jelly | 51.6 |
| Dist. water    q.s. to | 100.0 |

EXAMPLE 6

A 2% solution of the following composition is prepared in accordance with the art of pharmaceutical compounding:

| Ingredient | Weight in Grams |
|---|---|
| Vitamin A acid ethyl amide | 2 |
| Ethyl alcohol 94% | 70 |
| Propylene glycol    q.s. to | 100 |

EXAMPLE 7

Soft gelatin capsules of the following composition are prepared in accordance with the art of pharmaceutical compounding:

| Ingredient | Weight per capsule |
|---|---|
| Vitamin A acid ethyl amide | 20 mg |
| Wax mixture | 51.5 mg |
| Vegetable oil | 103.0 mg |
| Sequestrene[1] | 0.5 mg |
| Total Fill Weight | 175.0 mg |

[1]complexing agent-ethylenediaminetetra-acetic acid, sodium salt.

We claim:
1. A compound represented by the formula

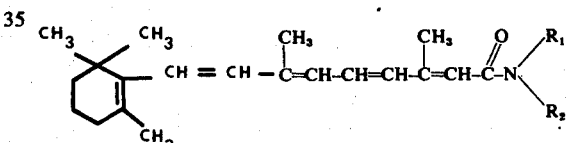

wherein $R_1$ is a lower alkoxy alkyl group and $R_2$ is hydrogen.

2. The compound of claim 1 wherein said compound is vitamin A acid 2-methoxyethyl amide.

3. A compound represented by the formula

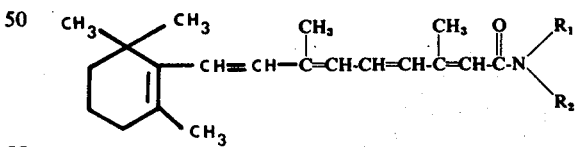

wherein $R_1$ is a hydroxy lower alkyl group and $R_2$ is hydrogen.

4. The compound of claim 3 wherein said compound is vitamin A acid ethanol amide.

5. A compound represented by the formula

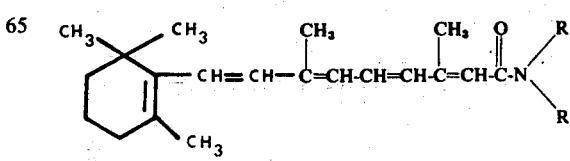

wherein R₁ is a lower alkylaminoalkyl group and R₂ is hydrogen.
6. The compound of claim 5 wherein said compound is vitamin A acid 2-diethylaminoethyl amide.
7. A compound represented by the formula
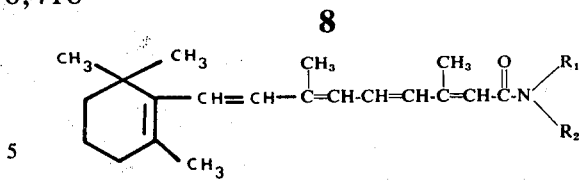
wherein R₁ is a hydroxy-lower alkylcyclohexyl group and R₂ is hydrogen.
8. The compound of claim 7 wherein said compound is vitamin A acid 2-hydroxyethyl cyclohexyl amide.
* * * * *